(12) United States Patent
Namiki

(10) Patent No.: US 10,614,565 B2
(45) Date of Patent: Apr. 7, 2020

(54) INSPECTION DEVICE AND INSPECTION SYSTEM

(71) Applicant: FANUC CORPORATION, Yamanashi (JP)

(72) Inventor: Yuta Namiki, Yamanashi (JP)

(73) Assignee: Fanuc Corporation, Yamanashi (JP)

(*) Notice: Subject to any disclaimer, the term of this patent is extended or adjusted under 35 U.S.C. 154(b) by 85 days.

(21) Appl. No.: 16/103,131

(22) Filed: Aug. 14, 2018

(65) Prior Publication Data

US 2019/0096055 A1 Mar. 28, 2019

(30) Foreign Application Priority Data

Sep. 27, 2017 (JP) .................................. 2017-186914

(51) Int. Cl.
*G06T 7/00* (2017.01)
*B25J 9/16* (2006.01)
(Continued)

(52) U.S. Cl.
CPC .......... *G06T 7/0004* (2013.01); *B25J 9/1664* (2013.01); *B25J 9/1679* (2013.01); *B25J 9/1697* (2013.01);
(Continued)

(58) Field of Classification Search
None
See application file for complete search history.

(56) References Cited

U.S. PATENT DOCUMENTS 4,922,338 A 5/1990 Arpino
6,321,137 B1 * 11/2001 De Smet ................ B25J 9/1692
700/245
(Continued)

FOREIGN PATENT DOCUMENTS

JP 2005-52926 3/2005
JP 2006-260271 9/2006
(Continued)

OTHER PUBLICATIONS

Notification of Reasons for Refusal dated Jun. 4, 2019 in Japanese Patent Application No. 2017-186914.

*Primary Examiner* — Andrae S Allison
(74) *Attorney, Agent, or Firm* — Wenderoth, Lind & Ponack, L.L.P.

(57) ABSTRACT

An inspection device includes: a line-of-sight information acquisition unit that acquires line-of-sight information including a starting point of a line of sight, a line-of-sight direction, and an observation range of an inspector during visual inspection; a target object information acquisition unit that acquires target object information including a position, an attitude, and a shape of the inspection target object during the visual inspection; and a program generation unit that specifies an observation position of the inspection target object observed by the inspector during the visual inspection as an inspection position based on the line-of-sight information and the target object information, captures an image of the specified inspection position of the inspection target object using the inspection imaging device, and generates an inspection execution program for performing inspection of the inspection target object based on the captured image of the inspection position of the inspection target object.

10 Claims, 10 Drawing Sheets

(51) Int. Cl.
*G06T 7/50* (2017.01)
*G06T 7/70* (2017.01)
*B25J 19/02* (2006.01)

(52) U.S. Cl.
CPC .............. *B25J 19/023* (2013.01); *G06T 7/50*
(2017.01); *G06T 7/70* (2017.01); *G06T*
*2207/20081* (2013.01); *G06T 2207/30108*
(2013.01)

(56) References Cited

U.S. PATENT DOCUMENTS

| | | | |
|---|---|---|---|
| 2004/0114033 A1* | 6/2004 | Eian ..................... | H04N 13/261 348/42 |
| 2006/0023938 A1* | 2/2006 | Ban ........................ | B25J 9/1692 382/153 |
| 2007/0150228 A1* | 6/2007 | Fukumoto .......... | G01B 11/2518 702/155 |
| 2010/0141776 A1* | 6/2010 | Ban ........................ | B25J 9/1692 348/187 |
| 2012/0191244 A1* | 7/2012 | Kim ....................... | B25J 9/1602 700/245 |
| 2012/0290513 A1* | 11/2012 | Frank ..................... | G06F 3/013 706/12 |
| 2015/0169824 A1* | 6/2015 | Kermani ................ | G16B 40/00 702/19 |
| 2015/0371388 A1* | 12/2015 | Ishida .................... | G06T 17/20 382/294 |
| 2017/0028562 A1* | 2/2017 | Yamazaki .............. | B25J 9/1612 |
| 2018/0222049 A1* | 8/2018 | Suzuki ................... | B25J 9/1692 |
| 2018/0349633 A1* | 12/2018 | Takimoto ............... | G06N 20/00 |

FOREIGN PATENT DOCUMENTS

| | | |
|---|---|---|
| JP | WO2007141857 A1 * | 10/2009 |
| JP | 2010-223932 | 10/2010 |
| JP | 2010223932 | * 10/2010 |
| JP | 2014-178229 | 9/2014 |
| JP | 2017-142739 | 8/2017 |
| WO | 2007/141857 | 12/2007 |

\* cited by examiner

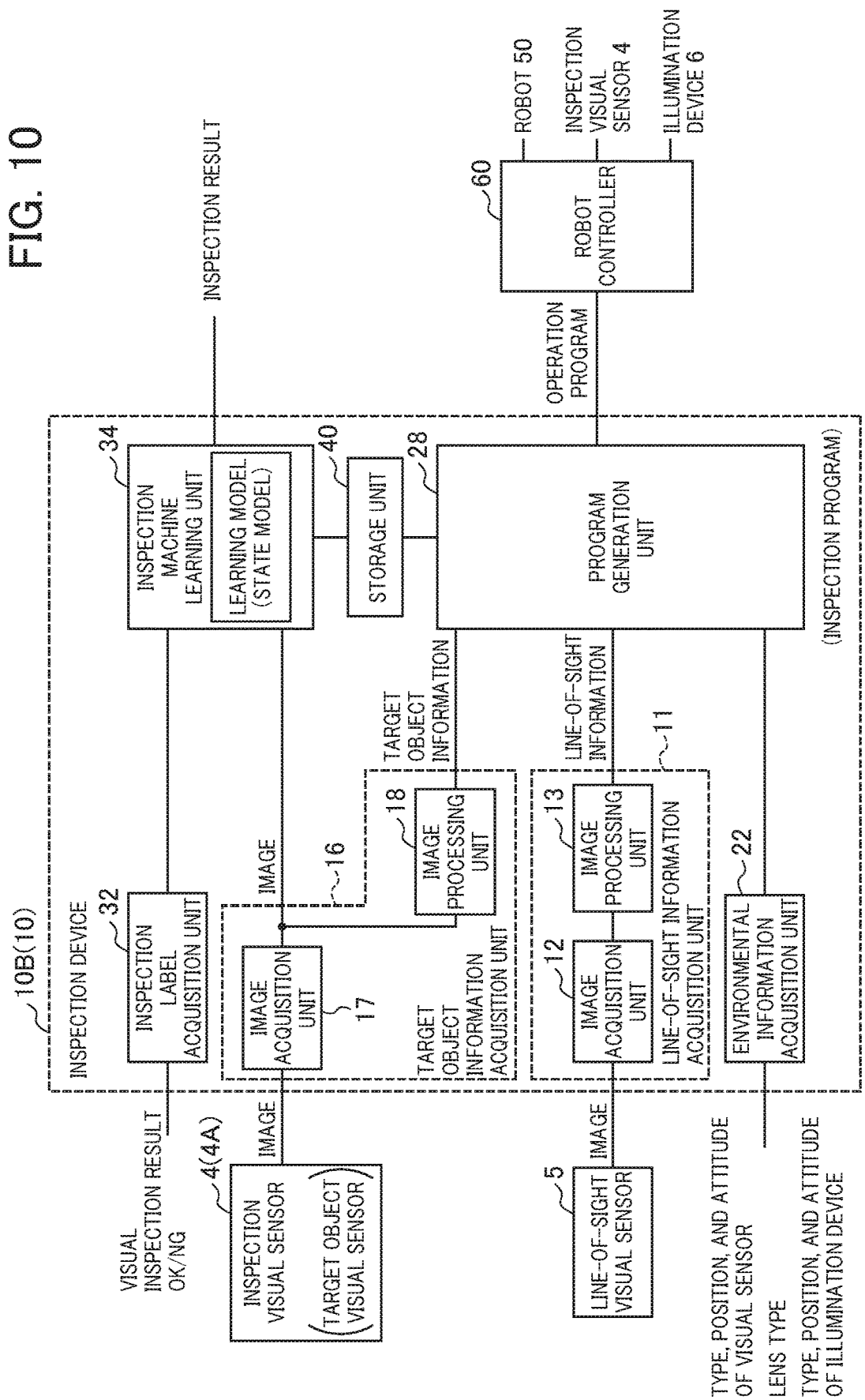

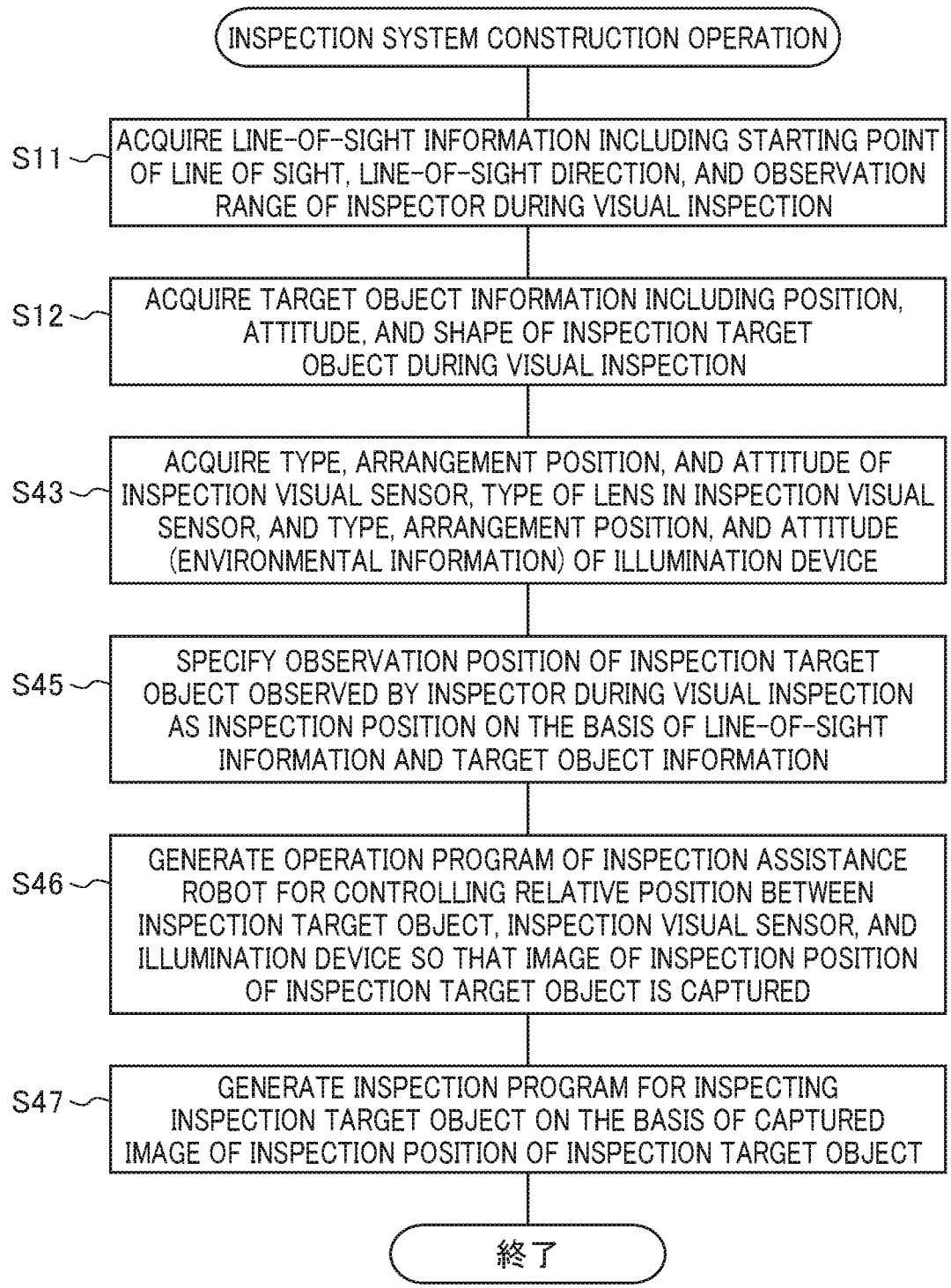

INSPECTION DEVICE AND INSPECTION SYSTEM

This application is based on and claims the benefit of priority from Japanese Patent Application No. 2017-186914, filed on 27 Sep. 2017, the content of which is incorporated herein by reference.

BACKGROUND OF THE INVENTION

Field of the Invention

The present invention relates to an inspection device and an inspection system for inspecting an inspection target object on the basis of an image of the inspection target object captured by an imaging device.

Related Art

An inspection system that automatically controls a relative position between an inspection target object and an imaging device using an inspection assistance robot and automatically inspects (for example, for presence of defects) the inspection target object on the basis of an image of the inspection target object captured by the imaging device is known. When such an inspection system is constructed, it is necessary to design the design value such as a positional relationship between the inspection target object and the imaging device, the type of the imaging device used, a positional relationship between the inspection target object and an illumination device, the type of the illumination device used, an operation program of the inspection assistance robot, an inspection program, and the like. Patent Documents 1 and 2 disclose methods for constructing such an inspection system.

In the inspection systems disclosed in Patent Documents 1 and 2, a virtual inspection target object is displayed on a screen of a display device on the basis of CAD data of the inspection target object, and an inspector designates an inspection position assuming that a display image of the virtual inspection target object is an inspection image captured by the imaging device. The position of the imaging device is calculated on the basis of the designated inspection position.

Patent Document 1: Japanese Unexamined Patent Application, Publication No. 2005-52926
Patent Document 2: Japanese Unexamined Patent Application, Publication No. 2006-260271

SUMMARY OF THE INVENTION

When an inspection system is constructed, it takes a considerable amount of time to design the design value for each type of the inspection target object and it is difficult for an inspector having no knowledge thereabout to do so.

An object of the present invention is to provide an inspection system and an inspection device for automatically constructing the inspection system easily.

(1) An inspection device (for example, an inspection device 10, 10A, 10B to be described later) according to the present invention is an inspection device that performs inspection of an inspection target object on the basis of an image of the inspection target object captured by an inspection imaging device (for example, an inspection visual sensor 4 to be described later), the inspection device including: a line-of-sight information acquisition unit (for example, a line-of-sight information acquisition unit 11 to be described later) that acquires line-of-sight information including a starting point of a line of sight, a line-of-sight direction, and an observation range of an inspector when the inspector performs visual inspection of the inspection target object; a target object information acquisition unit (for example, a target object information acquisition unit 16 to be described later) that acquires target object information including a position, an attitude, and a shape of the inspection target object during the visual inspection; and a program generation unit (for example, a program generation unit 28 to be described later) that specifies an observation position of the inspection target object observed by the inspector during the visual inspection as an inspection position on the basis of a set of pieces of data including the line-of-sight information and the target object information, captures an image of the specified inspection position of the inspection target object using the inspection imaging device, and generates an inspection execution program for performing inspection of the inspection target object on the basis of the captured image of the inspection position of the inspection target object.

(2) In the inspection device according to (1), the program generation unit may specify the inspection position of the inspection target object on the basis of a plurality of sets of pieces of data including the line-of-sight information and the target object information acquired at the same timing.

(3) In the inspection device according to (1) or (2), the inspection execution program may use an inspection assistance robot (for example, an inspection assistance robot 50 to be described later) that holds the inspection target object or the inspection imaging device using an arm, and may include an operation program of the inspection assistance robot for controlling a relative position between the inspection target object and the inspection imaging device so that an image of the inspection position of the inspection target object is captured using the inspection imaging device.

(4) In the inspection device according to any one of (1) to (3), the inspection execution program may include an inspection program for performing inspection of the inspection target object on the basis of the image of the inspection position of the inspection target object captured using the inspection imaging device.

(5) The inspection device according to (3) may further include: an environmental information acquisition unit (for example, an environmental information acquisition unit 22 to be described later) that acquires at least one of a type, an arrangement position, and an attitude of the inspection imaging device and a type of a lens in the inspection imaging device as environmental information, and the program generation unit may generate an operation program of the inspection assistance robot for controlling the relative position between the inspection target object and the inspection imaging device on the basis of the environmental information.

(6) The inspection device according to (3) or (5) may further include: an environmental information acquisition unit (for example, an environmental information acquisition unit 22 to be described later) that acquires at least one of a type, an arrangement position, and an attitude of an illumination device that illuminates the inspection target object as environmental information, and the program generation unit may generate an operation program of the inspection assistance robot for controlling a relative position between the inspection target object, the inspection imaging device, and the illumination device on the basis of the environmental information.

(7) The inspection device according to (3) may further include: an image acquisition unit (for example, an image acquisition unit 17 to be described later) that acquires the image of the inspection position of the inspection target object captured by the inspection imaging device; an inspection label acquisition unit (for example, an inspection label acquisition unit 32 to be described later) that acquires a label assigned to the image acquired by the image acquisition unit, the label indicating an inspection result of the inspection position of the inspection target object during the visual inspection; and an inspection machine learning unit (for example, an inspection machine learning unit 34 to be described later) that learns a learning model using the image acquired by the image acquisition unit as input data and using the label acquired by the inspection label acquisition unit as teaching data, and the inspection machine learning unit may perform inspection of the inspection target object on the basis of the image acquired by the image acquisition unit according to the learnt learning model.

(8) The inspection device according to any one of (1) to (3) may further include: an environmental information acquisition unit (for example, an environmental information acquisition unit 22 to be described later) that acquires environmental information on an environment during the visual inspection; a construction label acquisition unit (for example, a construction label acquisition unit 24 to be described later) that acquires a design value of an inspection system for automating the visual inspection using the inspection imaging device as a label; and a construction machine learning unit (for example, a construction machine learning unit 26 to be described later) that learns a learning model using the line-of-sight information acquired by the line-of-sight information acquisition unit, the target object information acquired by the target object information acquisition unit, and the environmental information acquired by the environmental information acquisition unit as input data and using the label acquired by the construction label acquisition unit as teaching data, and the construction machine learning unit may output the design value of the inspection system according to the learnt learning model on the basis of the line-of-sight information acquired by the line-of-sight information acquisition unit, the target object information acquired by the target object information acquisition unit, and the environmental information acquired by the environmental information acquisition unit during the visual inspection.

(9) In the inspection device according to (8), the inspection execution program may use an inspection assistance robot that holds the inspection target object or the inspection imaging device using an arm and may include an operation program of the inspection assistance robot for controlling a relative position between the inspection target object and the inspection imaging device so that an image of the inspection position of the inspection target object is captured using the inspection imaging device, the program generation unit may include the construction machine learning unit and specify an observation position of the inspection target object observed by the inspector during the visual inspection as an inspection position on the basis of a set of pieces of data including the line-of-sight information and the target object information, and the program generation unit may generate an operation program of the inspection assistance robot for controlling a relative position between the inspection target object and the inspection imaging device on the basis of the learning model learnt by the construction machine learning unit so that an image of the specified inspection position of the inspection target object is captured using the inspection imaging device.

(10) In the inspection device according to (9), the environmental information may include at least one of a type, an arrangement position, and an attitude of an illumination device that illuminates the inspection target object, and the program generation unit may generate an operation program of the inspection assistance robot for controlling a relative position between the inspection target object, the inspection imaging device, and the illumination device.

(11) In the inspection device according to (9) or (10), the design value of the inspection system may include at least one of a type, an arrangement position, and an attitude of the inspection imaging device, a type of an optical lens in the inspection imaging device, a type, an arrangement position, and an attitude of an illumination device that illuminates the inspection target object, an operation program of the inspection assistance robot, and an inspection program, and the program generation unit may generate an operation program of the inspection assistance robot for controlling a relative position between the inspection target object, the inspection imaging device, and the illumination device.

(12) In the inspection device according to (11), the operation program included in the design value of the inspection system may be a correction operation program obtained by correcting the operation program generated by the program generation unit.

(13) The inspection device according to any one of (9) to (12) may further include: an environmental information output unit (for example, an environmental information output unit 30 to be described later) that outputs environmental information on an environment in the design value of the inspection system output from the construction machine learning unit, and the environmental information may include at least one of the type, the arrangement position, and the attitude of the inspection imaging device and the type of the lens in the inspection imaging device.

(14) The inspection device according to any one of (9) to (13) may further include: an environmental information output unit (for example, an environmental information output unit 30 to be described later) that outputs environmental information on an environment in the design value of the inspection system output from the construction machine learning unit, and the environmental information may include at least one of the type, the arrangement position, and the attitude of the illumination device that illuminates the inspection target object.

(15) An inspection system (for example, an inspection system 1A, 1B to be described later) according to the present invention includes: the inspection device according to any one of (1) to (14); an inspection imaging device (for example, an inspection visual sensor 4 to be described later) that captures an image of an inspection target object; a line-of-sight imaging device (for example, a line-of-sight visual sensor 5 to be described later) that captures an image of an inspector to obtain line-of-sight information of the inspector when the inspector performs visual inspection of the inspection target object; a target object imaging device (for example, a target object imaging device 4A to be described later) that captures an image of the inspection target object to obtain target object information of the inspection target object during the visual inspection; an inspection assistance robot (for example, an inspection assistance robot 50 to be described later) that holds the inspection target object or the inspection imaging device and controls a relative position between the inspection target object and the inspection imaging device; a robot controller (for example, a robot controller 60 to be described later) that controls the inspection assistance robot according to an operation program of the inspection assistance robot of the inspection execution program generated by the inspection device; and an illumination device (for example, an illumination device 6 to be described later) that illuminates the inspection target object.

According to the present invention, it is possible to provide an inspection system and an inspection device capable of constructing the inspection system easily.

BRIEF DESCRIPTION OF THE DRAWINGS

FIG. 10 is a diagram illustrating a configuration of an inspection device according to a second embodiment.

FIG. 11 is a flowchart illustrating an inspection system construction operation performed by the inspection device according to the second embodiment.

DETAILED DESCRIPTION OF THE INVENTION

Figure 1A:
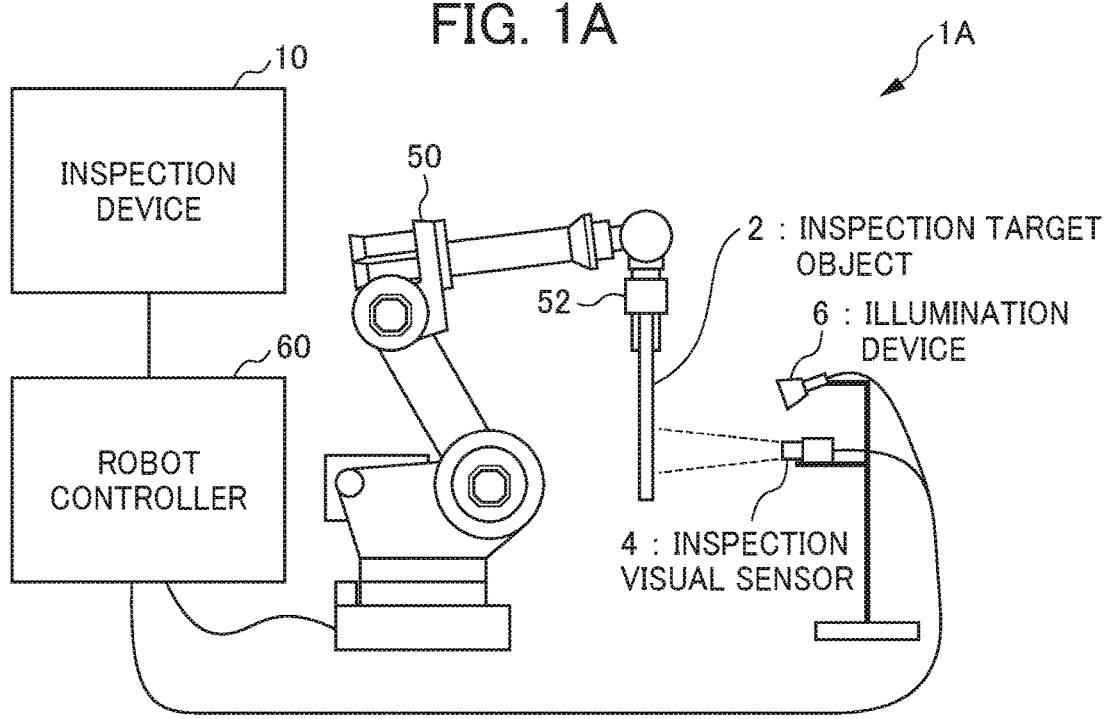
FIG. 1A is a diagram illustrating a configuration of an inspection system according to the present embodiment.

Hereinafter, an example of an embodiment of the present invention will be described with reference to the accompanying drawings. The same or corresponding portions in the respective drawings will be denoted by the same reference numerals.

Figure 1B:
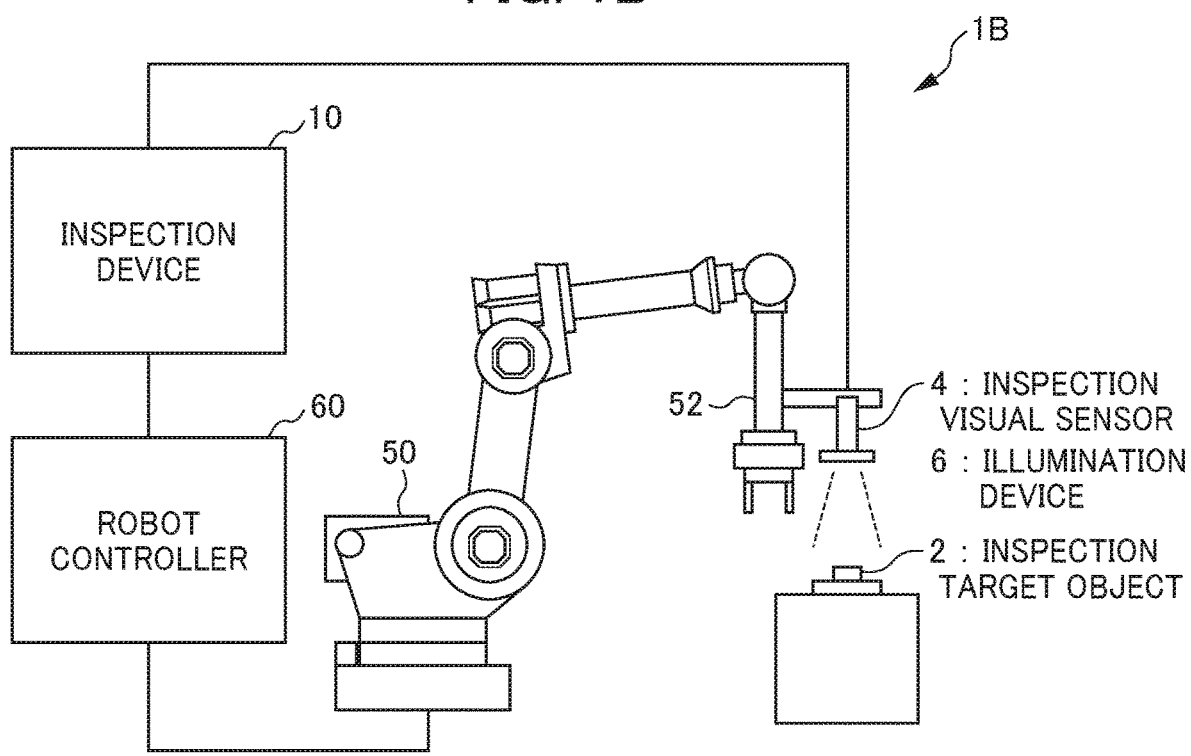
FIG. 1B is a diagram illustrating a configuration of another inspection system according to the present embodiment.

FIG. 1A is a diagram illustrating a configuration of an inspection system according to the present embodiment, and FIG. 1B is a diagram illustrating a configuration of another inspection system according to the present embodiment. These inspection systems 1A and 1B are systems that inspect for the presence of defects (for example, scratches on a surface or adhesion of foreign materials) of an inspection target object 2 on the basis of an image of the inspection target object 2 captured by an inspection visual sensor 4, for example.

The inspection system 1A illustrated in FIG. 1A includes the inspection visual sensor 4, an illumination device 6, an inspection device 10, an inspection assistance robot 50, and a robot controller 60. The inspection visual sensor 4 captures an image of the inspection target object 2 and provides the captured image of the inspection target object 2 to the inspection device 10. The inspection visual sensor 4 can replace the type of an optical lens included therein. The illumination device 6 illuminates the inspection target object 2. The inspection assistance robot 50 grasps the inspection target object 2 using the hand of an arm 52. The robot controller 60 executes an inspection assistance robot operation program and controls the inspection assistance robot 50 to control the position and the attitude of the inspection target object 2. In this manner, in the inspection system 1A, the position and the attitude of the inspection target object 2 are controlled while fixing the position and the attitude of the inspection visual sensor 4 and the position of the illumination device 6 to thereby control the relative position between the inspection target object 2, the inspection visual sensor 4, and the illumination device 6. The inspection device 10 executes an inspection program, inspects for the presence of defects of the inspection target object 2 on the basis of the image of the inspection target object 2 captured by the inspection visual sensor 4, and outputs the inspection results to an external device. In the present embodiment, the operation program of the inspection assistance robot and the inspection program of the inspection device form an inspection execution program.

On the other hand, the inspection system 1B illustrated in FIG. 1B is different from the inspection system 1A illustrated in FIG. 1A in that the inspection assistance robot 50 holds the inspection visual sensor 4 and the illumination device 6 instead of the inspection target object 2. The inspection assistance robot 50 holds the inspection visual sensor 4 and the illumination device 6 at the distal end of the arm 52. The robot controller 60 executes an inspection assistance robot operation program and controls the inspection assistance robot 50 to control the position and the attitude of the inspection visual sensor 4 and the position of the illumination device 6. In this manner, in the inspection system 1B, the position and the attitude of the inspection visual sensor 4 and the position of the illumination device 6 are controlled while fixing the position and the attitude of the inspection target object 2 to thereby control the relative position between the inspection target object 2, the inspection visual sensor 4, and the illumination device 6. Hereinafter, the inspection device 10 will be described in detail.

Figure 2:
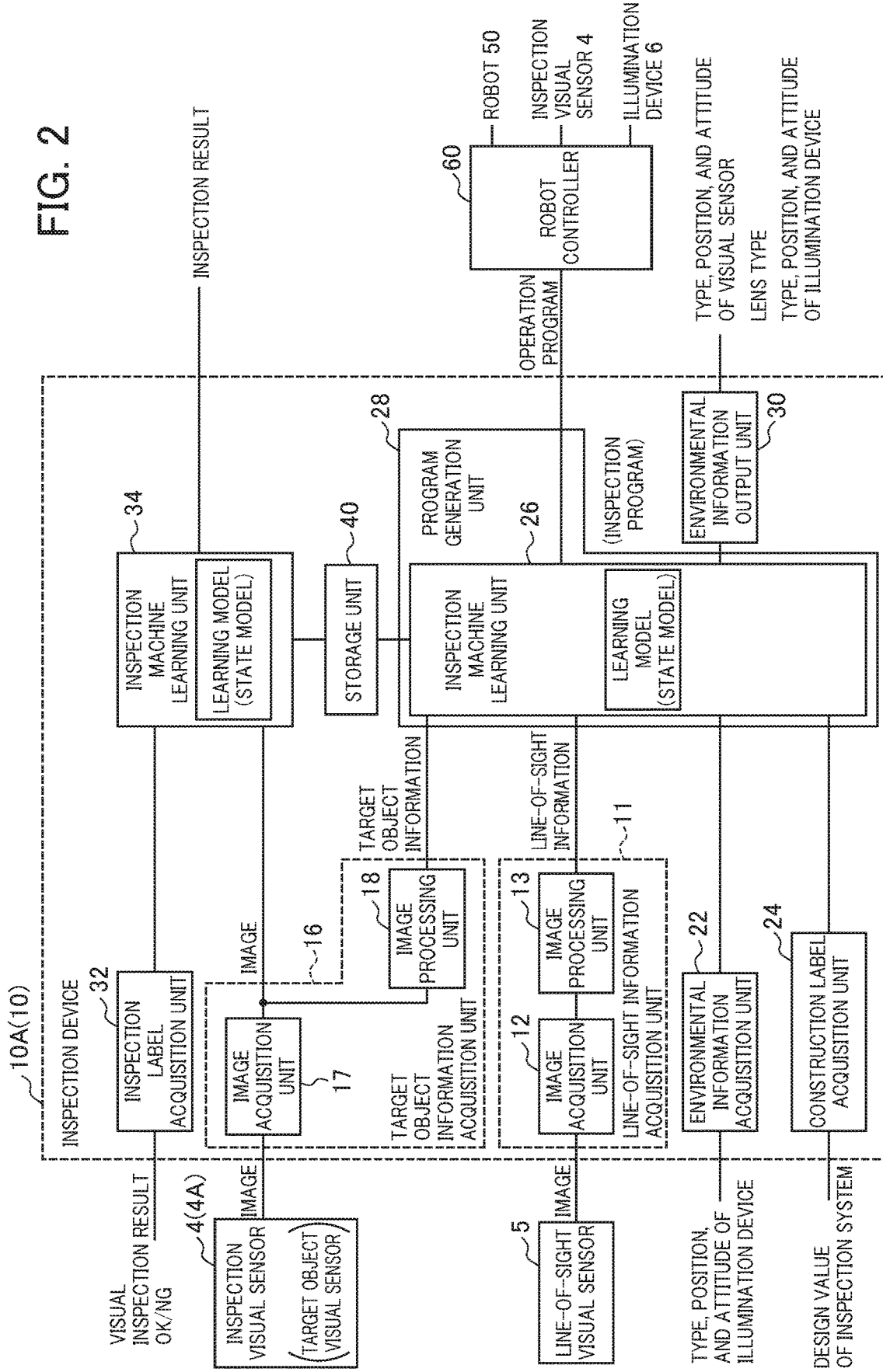
FIG. 2 is a diagram illustrating a configuration of an inspection device according to a first embodiment.

FIG. 2 is a diagram illustrating a configuration of an inspection device according to the first embodiment. An inspection device 10A illustrated in FIG. 2 corresponds to the inspection device 10 of the inspection systems 1A and 1B illustrated in FIGS. 1A and 1B, respectively.

Figure 3:
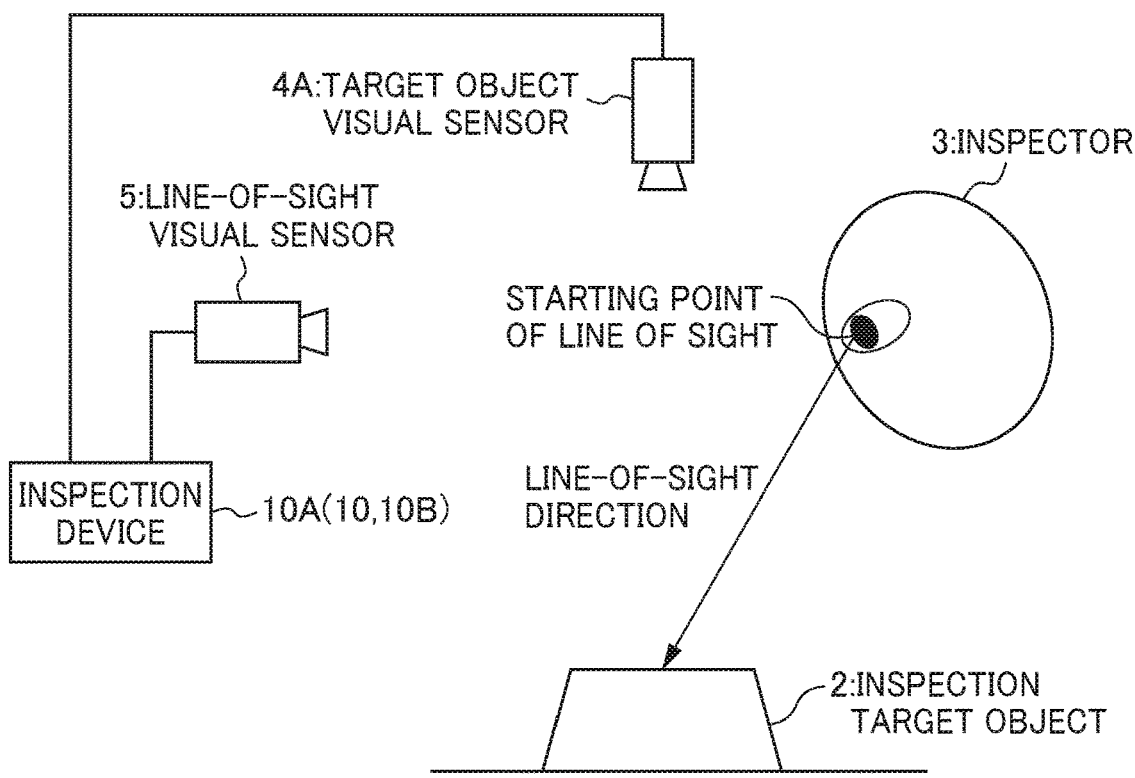
FIG. 3 is a schematic diagram for describing visual inspection.

The inspection device 10A automatically constructs an inspection system for automating visual inspection that an inspector 3 performs to inspect for defects of the inspection target object 2 with the naked eyes using a line-of-sight visual sensor 5. Specifically, as illustrated in FIG. 3, the inspection device 10A automatically constructs an inspection system using an image of the vicinity of the eyes of the inspector 3 captured by the line-of-sight visual sensor 5 and an image of the inspection target object 2 captured by a target object visual sensor 4A when the inspector 3 performs visual inspection for defects of the inspection target object 2.

The target object visual sensor 4A captures an image of the inspection target object 2 and provides the captured image of the inspection target object 2 to the inspection device 10A. In the present embodiment, although an aspect in which the inspection visual sensor 4 also serves as the target object visual sensor 4A is illustrated, the target object visual sensor 4A may be another visual sensor other than the inspection visual sensor 4.

The line-of-sight visual sensor 5 captures an image of the vicinity of the eyes of the inspector 3 and provides the captured image of the vicinity of the eyes of the inspector 3 to the inspection device 10A. In the present embodiment, although the image of the vicinity of the eyes of the inspector 3 and the image of the inspection target object 2 are captured by two visual sensors, respectively, the image of the vicinity of the eyes of the inspector 2 and the image of the inspection target object 2 may be captured by one visual sensor.

After an inspection system is constructed, the inspection device 10A automatically inspects for defects of the inspection target object 2 on the basis of the image of the inspection target object 2 captured by the inspection visual sensor 4.

The inspection device 10A includes a line-of-sight information acquisition unit 11, a target object information acquisition unit 16, an environmental information acquisition unit 22, a construction label acquisition unit 24, a program generation unit 28 including a construction machine learning unit 26, an environmental information output unit 30, an inspection label acquisition unit 32, an inspection machine learning unit 34, and a storage unit 40.

Figure 4:
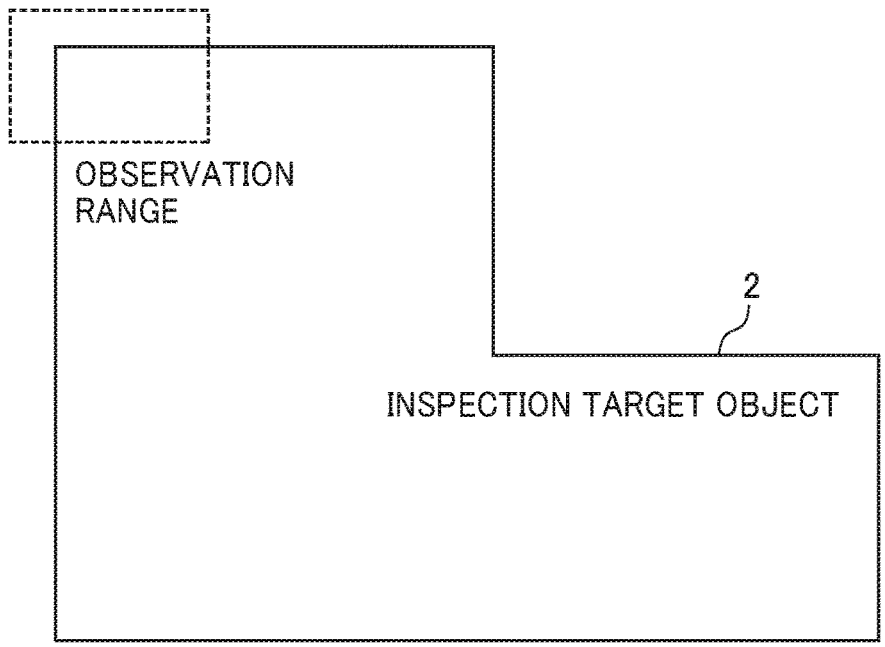
FIG. 4 is a schematic diagram illustrating an observation range of an inspection target object.

The line-of-sight information acquisition unit 11 includes an image acquisition unit 12 and an image processing unit 13. The image acquisition unit 12 is a communication interface, for example, and receives the image captured by the line-of-sight visual sensor 5. As illustrated in FIG. 3, the image processing unit 13 performs image processing of the received image to calculate the position of the eyeball of the inspector 3 as the starting point of the line of sight and calculate the line-of-sight direction of the inspector 3. As illustrated in FIG. 4, the image acquisition unit (the communication interface) 12 of the line-of-sight information acquisition unit 11 receives an observation range of the inspection target object 2 during visual inspection, the observation range (a fixed value) being input in advance by the inspector. The line-of-sight information acquisition unit 11 may change the size of the observation range according to the distance between the inspection target object 2 and the starting point of the line of sight. In this way, the line-of-sight information acquisition unit 11 acquires the line-of-sight information including the starting point of the line of sight, the line-of-sight direction, and the observation range (the fixed value) of the inspector 3 when the inspector 3 performs visual inspection for defects of the inspection target object 2.

The target object information acquisition unit 16 includes an image acquisition unit 17 and an image processing unit 18. The image acquisition unit 17 is a communication interface, for example, and receives the image captured by the target object visual sensor 4A. The image processing unit 18 performs image processing of the received image and calculates the position, the attitude, and the shape of the inspection target object 2. The target object information acquisition unit 16 may receive CAD information and calculate the shape of the inspection target object 2 on the basis of the CAD information. If the position of the inspection target object 2 is fixed, the image acquisition unit (the communication interface) 17 of the target object information acquisition unit 16 may receive the position and the attitude (fixed values) of the inspection target object 2 input in advance by the inspector. In this way, the target object information acquisition unit 16 acquires the target object information including the position, the attitude, and the shape of the inspection target object 2 when the inspector performs visual inspection of the inspection target object 2.

The line-of-sight information acquisition unit 11 and the target object information acquisition unit 16 acquires the line-of-sight information and the target object information from the images captured at the same timing by the line-of-sight visual sensor 5 and the target object visual sensor 4A. In the present embodiment, it is assumed that the timing at which the line-of-sight information and the target object information are acquired is designated by the inspector 3. For example, the acquisition timing may be the timing at which the inspector 3 presses a predetermined operation button and may be the timing at which the inspector 3 performs a predetermined gesture such as closing the eyes for several seconds. The positions and the attitudes acquired by the line-of-sight information acquisition unit 11, the target object information acquisition unit 16, and the environmental information acquisition unit 22 to be described later are represented on the same coordinate system. For that, the relative positional relationship between the line-of-sight visual sensor 11 and the target object visual sensor 16 needs to be known.

The environmental information acquisition unit 22 acquires the type, the arrangement position, and the attitude of the illumination device 6 as the environmental information on the environment during the visual inspection. The environmental information may be input by the inspector, for example, and may be acquired from the information (the design value of the inspection system to be described later) during designing of the inspection system.

The construction label acquisition unit 24 acquires the design value of the inspection system for automating visual inspection using the inspection visual sensor 4 as a label. The design value of the inspection system includes the type, the arrangement position, and the attitude of the inspection visual sensor 4, the type of an optical lens in the inspection visual sensor 4, the type, the arrangement position, and the attitude of the illumination device 6, the operation program of the inspection assistance robot, and the inspection program of the inspection device.

A plurality of sets of pieces of data including the line-of-sight information, the target object information, the environmental information, and the label acquired at the same timing are temporarily stored in the storage unit 40 as learning data.

During machine learning, the construction machine learning unit 26 learns a learning model (a state model) on the basis of the plurality of sets of pieces of learning data including the line-of-sight information, the target object information, the environmental information, and the label temporarily stored in the storage unit 40. That is, the construction machine learning unit 26 learns a learning model using the line-of-sight information, the target object information (or the observation position), and the environmental information as input data and using the label as teaching data. The observation position may be used as the input data instead of the line-of-sight information and the target object information. The observation position is calculated in the following manner. The observation position of the inspection target object 2 observed by the inspector during visual inspection is specified as the inspection position on the basis of the line-of-sight information and the target object information acquired at the same timing. An observation point can be calculated as a point at which the line of sight of the inspector 3 crosses the surface of the inspection target object 2. When the observation range is provided around the observation point, it is the observation position. When the inspection system is constructed, the construction machine learning unit 26 outputs the design value of the inspection system according to the learnt learning model on the basis of the line-of-sight information acquired by the line-of-sight information acquisition unit 11, the target object information acquired by the target object information acquisition unit 16, and the environmental information acquired by the environmental information acquisition unit 22 during visual inspection. The construction machine learning unit 26 performs machine learning according to a learning model constructed by a neural network including a multilayer neural network, for example. A learning model constructed by a neural network including an input layer, an output layer, and an intermediate layer can employ an appropriate scheme. For example, a convolutional neural network (CNN) can be employed.

During machine learning, the construction machine learning unit 26 can further perform learning using the operation program of the inspection assistance robot as a label. By doing so, the program generation unit 28 can perform inference using a learning model learnt using the environmental information and the line-of-sight information and the target object information (or the observation position) newly acquired by the construction machine learning unit 26 as input data and can output an operation program of the inspection assistance robot. The output operation program of the inspection assistance robot can be used by an inspection system constructed on the basis of the output design value of the inspection system. During machine learning, the construction machine learning unit 26 can further perform learning using the inspection program of the inspection device as a label. By doing so, the program generation unit 28 can perform inference using a learning model learnt using the environmental information and the line-of-sight information and the target object information (or the observation position) newly acquired by the construction machine learning unit 26 and can output an inspection program of the inspection device. The output inspection program of the inspection device can be used by an inspection system constructed on the basis of the output design value of the inspection system.

The environmental information output unit 30 outputs information on the type, the arrangement position, and the attitude of the inspection visual sensor 4, the type of the optical lens in the inspection visual sensor 4, and the type, the arrangement position, and the attitude of the illumination device 6 as the environmental information in the design value of the inspection system output from the construction machine learning unit 26. In this way, a person who constructs the inspection system can prepare the inspection visual sensor 4, the appropriate optical lens in the inspection visual sensor 4, and the illumination device 6.

The inspection label acquisition unit 32 acquires a label assigned to the image of the inspection position of the inspection target object 2 acquired by the image acquisition unit 17, the label indicating the inspection result (for example, OK (no defects) or NG (with defects)) on the presence of defects of the inspection position of the inspection target object 2 during visual inspection by the inspector. The inspection result may be assigned at the same timing as the acquisition of the line-of-sight information and may be assigned while watching the image of the inspection position after all pieces of line-of-sight information are acquired.

A plurality of sets of pieces of data including the label and the images of the inspection position of the inspection target object 2 acquired at the same timing are temporarily stored in the storage unit 40 as learning data.

During machine learning, the inspection machine learning unit 34 learns a learning model (a state model) on the basis of the plurality of sets of pieces of learning data including the label and the images of the inspection position of the inspection target object 2 stored temporarily in the storage unit 40. That is, the inspection machine learning unit 34 learns a learning model using the images of the inspection position of the inspection target object 2 acquired by the image acquisition unit 17 as input data and using the label acquired by the inspection label acquisition unit 32 as teaching data. The learning model is included in the inspection program, for example. During inspection, the inspection machine learning unit 34 outputs an inspection result on the presence of defects of the inspection position of the inspection target object 2 on the basis of the image acquired by the image acquisition unit 17 according to the learnt learning model.

The storage unit 40 stores the learning data for the construction machine learning unit 26 and the learning data for the inspection machine learning unit 34. The storage unit 40 is a rewritable memory such as EEPROM, for example.

The image processing unit 13 of the line-of-sight information acquisition unit 11, the image processing unit 18 of the target object information acquisition unit 16, the environmental information acquisition unit 22, the construction label acquisition unit 24, the construction machine learning unit 26, the program generation unit 28, the environmental information output unit 30, the inspection label acquisition unit 32, and the inspection machine learning unit 34 of the inspection device 10A (and the inspection device 10B to be described later) are configured with an arithmetic processor such as a digital signal processor (DSP) or a field-programmable gate array (FPGA), for example. Various functions of the inspection device 10A (and the inspection device 10B to be described later) are realized by executing predetermined software (programs, applications) stored in a storage unit, for example. Various functions of the inspection device 10A (and the inspection device 10B to be described later) may be realized by cooperation of hardware and software and may be realized by hardware (electronic circuits) only.

Figure 5:
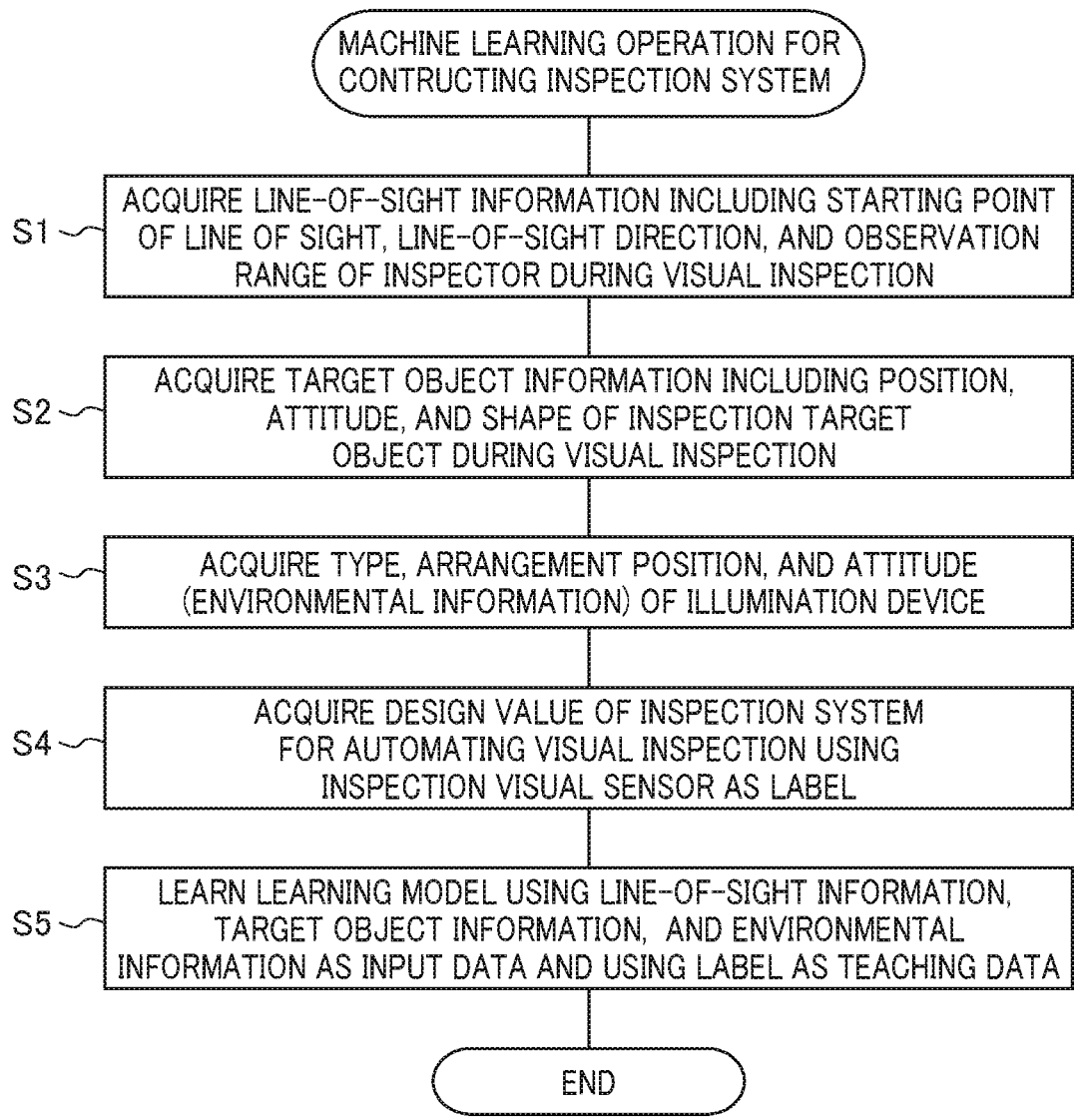
FIG. 5 is a flowchart illustrating a machine learning operation for allowing an inspection device according to the first embodiment to construct an inspection system.

Next, a machine learning operation for allowing the inspection device 10A of the present embodiment to construct an inspection system will be described with reference to FIGS. 3 to 5. FIG. 5 is a flowchart illustrating a machine learning operation for allowing the inspection device 10A of the present embodiment to construct an inspection system.

First, as illustrated in FIG. 3, when the inspector 3 performs visual inspection of the inspection target object 2, an image of the vicinity of the eyes of the inspector 3 is captured by the line-of-sight visual sensor 5, and an image of the inspection target object 2 is captured by the target object visual sensor 4A. The inspection target object 2 may be fixed and may be grasped by the inspector 3. In this case, the inspector inputs the type, the arrangement position, and the attitude of the illumination device 6 to the inspection device 10A as the environmental information during visual inspection. Moreover, the inspector inputs the type, the arrangement position, and the attitude of the inspection visual sensor 4, the type of the optical lens in the inspection visual sensor 4, the type, the arrangement position, and the attitude of the illumination device 6, the operation program of the inspection assistance robot, and the inspection program of the inspection device to the inspection device 10A as the design value of the inspection system for automating the visual inspection using the inspection visual sensor 4. As illustrated in FIG. 4, the inspector inputs an observation range (a fixed value) of the inspection target object 2 during visual inspection in advance.

The line-of-sight information acquisition unit 11 receives the image of the vicinity of the eyes of the inspector captured by the line-of-sight visual sensor 5 and performs image processing of the received image to calculate the starting point of a line of sight and the line-of-sight direction of the inspector 3. Moreover, the line-of-sight information acquisition unit 11 receives the observation range (a fixed value) input in advance by the inspector. In this way, the line-of-sight information acquisition unit 11 acquires line-of-sight information including the starting point of the line of sight, the line-of-sight direction, and the observation range (a fixed value) of the inspector 3 during visual inspection (S1). In this case, the target object information acquisition unit 16 receives the image of the inspection target object 2 captured by the target object visual sensor 4A and performs image processing of the received image to calculate the target object information including the position, attitude, and shape of the inspection target object 2. In this way, the target object information acquisition unit 16 acquires target object information including the position, attitude, and shape of the inspection target object 2 during visual inspection (S2). The line-of-sight information acquisition unit 11 and the target object information acquisition unit 16 acquires the line-of-sight information and the target object information from the images captured at the same timing by the line-of-sight visual sensor 5 and the target object visual sensor 4A.

The environmental information acquisition unit 22 acquires the type and the arrangement position and attitude (environmental information) of the illumination device 6 input by the inspector (S3). The construction label acquisition unit 24 acquires the type, the arrangement position, and the attitude of the inspection visual sensor 4, the type of the optical lens in the inspection visual sensor 4, the type, the arrangement position, and the attitude of the illumination device 6, the operation program of the inspection assistance robot, and the inspection program of the inspection device (the design value of the inspection system) input by the inspector as a label (S4). A plurality of sets of pieces of data including the line-of-sight information, the target object information, the environmental information, and the label acquired at the same timing are temporarily stored in the storage unit 40 as the learning data.

Subsequently, the construction machine learning unit 26 learns a learning model (a state model) on the basis of the plurality of sets of pieces of learning data including the line-of-sight information, the target object information, the environmental information, and the label temporarily stored in the storage unit 40. That is, the construction machine learning unit 26 learns a learning model using the line-of-sight information, the target object information, and the environmental information as input data and using the label as teaching data (S5). When there are a number of inspection positions of the inspection target object 2 during visual inspection, the above-described operation is performed for respective inspection positions.

The inspection assistance robot operation program in the design value of the inspection system that the construction label acquisition unit 24 acquires as the label may be a correction operation program obtained by the inspector correcting the inspection assistance robot operation program generated by the program generation unit 28 when the inspection system to be described later is constructed. That is, the inspection assistance robot operation program generated by performing the machine learning operation for construction of an inspection system in FIG. 5 and the inspection system construction operation in FIG. 6 to be described later may be corrected, and the machine learning operation for construction of the inspection system in FIG. 5 and the inspection system construction operation in FIG. 6 may be performed again. In this way, a more appropriate inspection assistance robot operation program may be generated.

Figure 6:
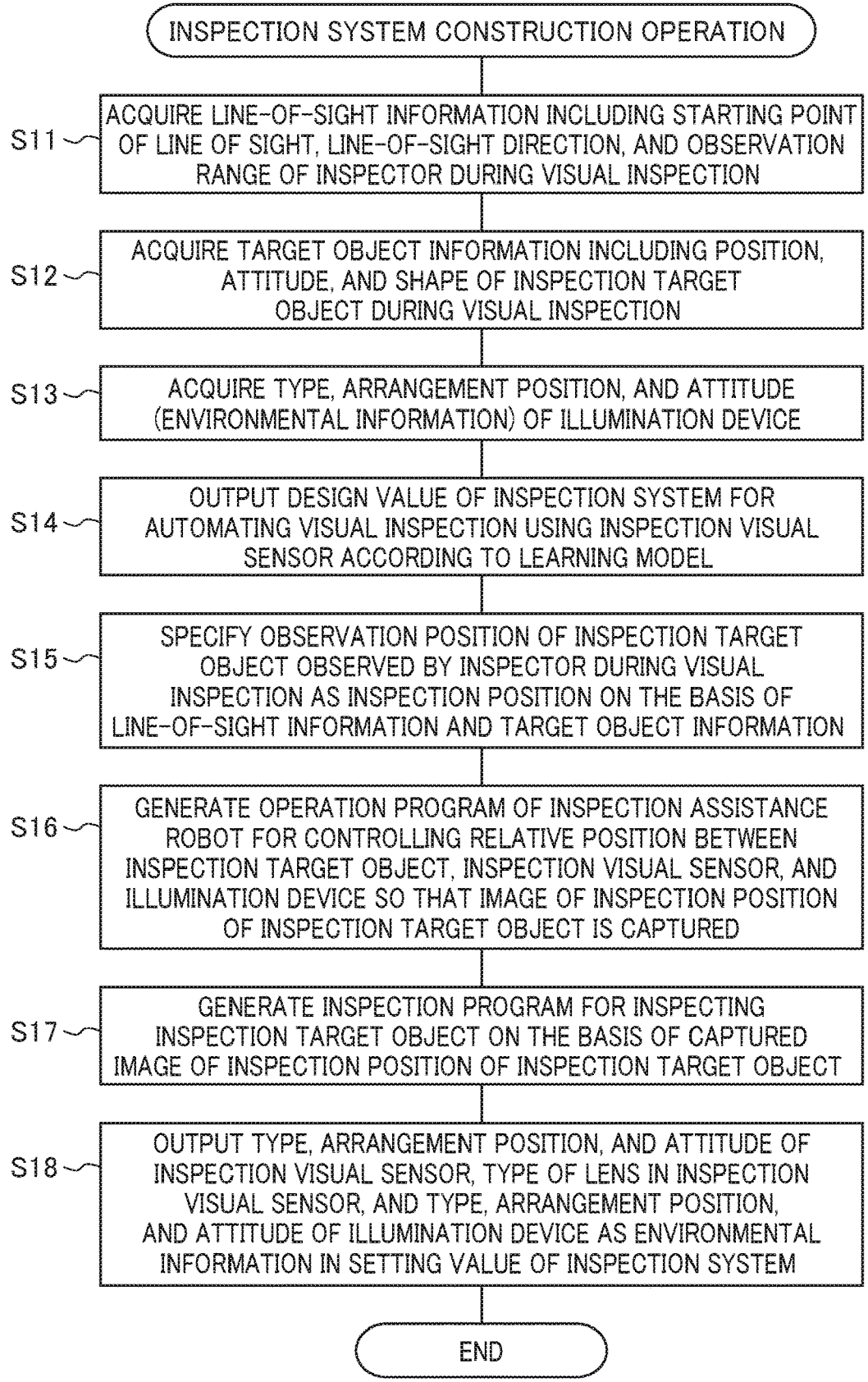
FIG. 6 is a flowchart illustrating an inspection system construction operation performed by the inspection device according to the first embodiment.

Next, an inspection system construction operation performed by the inspection device 10A of the present embodiment will be described with reference to FIGS. 3, 4, and 6. FIG. 6 is a flowchart illustrating an inspection system construction operation performed by the inspection device 10A of the present embodiment.

After the machine learning for constructing the inspection system described above ends, as illustrated in FIG. 3, when the inspector 3 newly performs visual inspection of the inspection target object 2, an image of the vicinity of the eyes of the inspector 3 is captured by the line-of-sight visual sensor 5 and an image of the inspection target object 2 is captured by the target object visual sensor 4A. In this case, the inspector inputs the type, the arrangement position, and the attitude of the illumination device 6 to the inspection device 10A as the environmental information during visual inspection. As illustrated in FIG. 4, the inspector inputs the observation range (a fixed value) of the inspection target object 2 during visual inspection in advance.

The line-of-sight information acquisition unit 11 receives the image of the vicinity of the eyes of the inspector captured by the line-of-sight visual sensor 5 and processes the received image to calculate the starting point of the line of sight and the line-of-sight direction of the inspector 3. Moreover, the line-of-sight information acquisition unit 11 receives the observation range (the fixed value) input in advance by the inspector. In this way, the line-of-sight information acquisition unit 11 acquires the line-of-sight information including the starting point of the line of sight, the line-of-sight direction, and the observation range (a fixed value) of the inspector 3 during visual inspection (S11). In this case, the target object information acquisition unit 16 receives the image of the inspection target object 2 captured by the target object visual sensor 4A and processes the received image to calculate the target object information including the position, attitude, and shape of the inspection target object 2. In this way, the target object information acquisition unit 16 acquires the target object information including the position, attitude, and shape of the inspection target object 2 during visual inspection (S12). The environmental information acquisition unit 22 acquires the type and the arrangement position and attitude (environmental information) of the illumination device input by the inspector (S13).

Subsequently, the construction machine learning unit 26 outputs the design value of the inspection system according to the learnt learning model on the basis of the line-of-sight information acquired by the line-of-sight information acquisition unit 11, the target object information acquired by the target object information acquisition unit 16, and the environmental information acquired by the environmental information acquisition unit 22. That is, the construction machine learning unit 26 outputs the type, the arrangement position, and the attitude of the inspection visual sensor 4, the type of an optical lens in the inspection visual sensor 4, the type, the arrangement position, and the attitude of the illumination device 6, the operation program of the inspection assistance robot, and the inspection program of the inspection device as the design value of the inspection system (S14).

Subsequently, the construction machine learning unit 26 (the program generation unit 28) specifies the observation position of the inspection target object 2 observed by the inspector during visual inspection as the inspection position on the basis of the line-of-sight information and the target object information acquired at the same timing (S15).

Subsequently, the program generation unit 28 performs inference using the learning model learnt by the construction machine learning unit 26 and generates an operation program of the inspection assistance robot. Specifically, the program generation unit 28 generates the operation program of the inspection assistance robot for controlling the relative position between the inspection target object 2, the inspection visual sensor 4, and the illumination device 6 so that the image of the specified inspection position of the inspection target object 2 is captured from an appropriate field of view and an appropriate distance using the inspection visual sensor 4. The relative position between the inspection target object 2 and the inspection visual sensor 4 may be controlled so that the image of the inspection target object 2 is captured in an appropriate size and may be controlled so that the image of the inspection target object 2 is captured in a certain size.

The program generation unit 28 performs inference using the learning model learnt by the construction machine learning unit 26 and generates an inspection program of the inspection device. Specifically, the program generation unit 28 generates an inspection program for inspecting the inspection target object 2 on the basis of the captured image of the inspection position of the inspection target object 2 (S17). When there are a number of inspection positions of the inspection target object 2, the program generation unit 28 generates the inspection assistance robot operation program and the inspection program so that all inspection positions are inspected sequentially. The inspection order may be the order of visual inspection performed by the inspector or may be the order in which a certain index becomes better (for example, the moving distance of the inspection assistance robot is the smallest).

In this case, the environmental information output unit 30 outputs the information on the type, the arrangement position, and the attitude of the inspection visual sensor 4, the type of the optical lens in the inspection visual sensor 4, and the type, the arrangement position, and the attitude of the illumination device 6 as the environmental information in the setting value of the inspection system output by the construction machine learning unit 26 (S18). In this way, the inspector can prepare the inspection visual sensor 4, the optical lens in the inspection visual sensor 4, and the illumination device 6.

Figure 7:
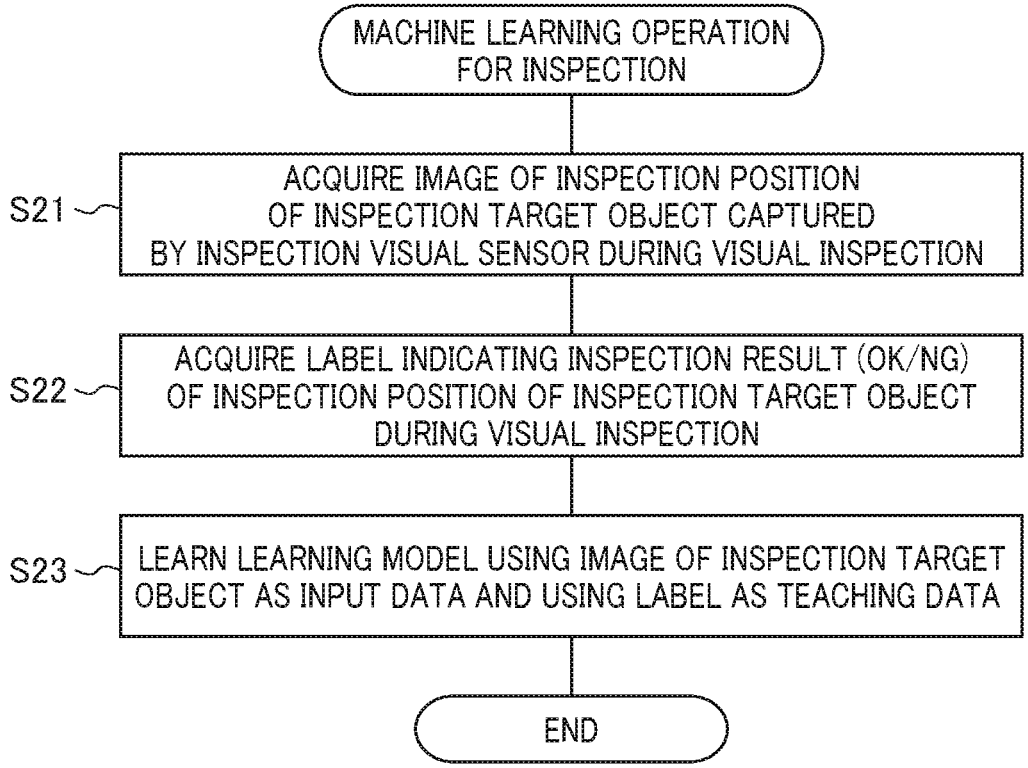
FIG. 7 is a flowchart illustrating a machine learning operation for allowing the inspection device according to the first embodiment to perform inspection.

Next, a machine learning operation for allowing the inspection device 10A of the present embodiment to perform inspection will be described with reference to FIG. 7. FIG. 7 is a flowchart illustrating the machine learning operation for allowing the inspection device 10A of the present embodiment to perform inspection.

After the inspection system is constructed, the inspector prepares and installs the inspection visual sensor 4, the optical lens in the inspection visual sensor 4, and the illumination device 6 on the basis of the type, the arrangement position, and the attitude of the inspection visual sensor 4, the type of the optical lens in the inspection visual sensor 4, and the type, the arrangement position, and the attitude of the illumination device 6 output by the environmental information output unit 30. The robot controller 60 drives and controls the inspection assistance robot 50 by executing the inspection assistance robot operation program generated by the program generation unit 28 and controls the relative position between the inspection target object 2, the inspection visual sensor 4, and the illumination device 6. The inspection visual sensor 4 captures the image of the inspection position of the inspection target object 2. The inspector inputs the inspection result (for example, OK (no defects) or NG (with defects)) on the presence of defects of the inspection position of the inspection target object 2 during visual inspection to the inspection device 10A.

The image acquisition unit 17 acquires the image of the inspection position of the inspection target object 2 captured by the inspection visual sensor 4 (S21). The inspection label acquisition unit 32 acquires a label assigned to the image of the inspection position of the inspection target object 2 acquired by the image acquisition unit 17, the label indicating the inspection result (for example, OK or NG) on the presence of defects of the inspection position of the inspection target object 2 during visual inspection by the inspector (S22). Simultaneously with the timing at which the inspection label acquisition unit 32 acquires the label of the inspection position of the inspection target object 2, the image acquisition unit 17 may acquire the image of the inspection position of the inspection target object 2. Alternatively, after the inspection label acquisition unit 32 acquires the labels of all inspection positions of the inspection target object 2, the constructed inspection system may automatically acquire the images of all inspection positions of the inspection target object 2. Data which is a set of sets of the acquired label and the image of the inspection position of the inspection target object 2 is temporarily stored in the storage unit 40 as learning data.

The inspection machine learning unit 34 learns a learning model (a state model) on the basis of the learning data which is a group of sets of the label and the image of the inspection position of the inspection target object 2 temporarily stored in the storage unit 40. That is, the inspection machine learning unit 34 learns a learning model using the images of the inspection position of the inspection target object 2 acquired by the image acquisition unit 17 as input data and using the label acquired by the inspection label acquisition unit 32 as teaching data (S23).

Figure 8:
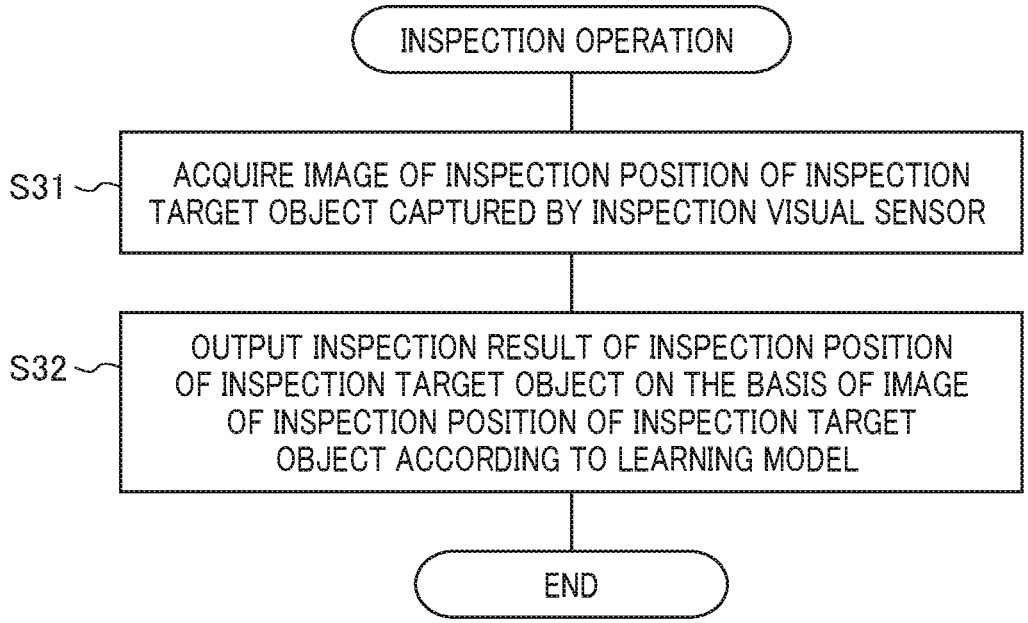
FIG. 8 is a flowchart illustrating an inspection operation performed by the inspection device according to the first embodiment.

Next, an inspection operation performed by the inspection device 10A of the present embodiment will be described with reference to FIG. 8. FIG. 8 is a flowchart illustrating an inspection operation performed by the inspection device 10A of the present embodiment.

After machine learning for inspection ends, the robot controller 60 drives and controls the inspection assistance robot 50 by executing the inspection assistance robot operation program again and controls the relative position between the inspection target object 2, the inspection visual sensor 4, and the illumination device 6. The inspection visual sensor 4 captures the image of the inspection position of the inspection target object 2.

The image acquisition unit 17 acquires the image of the inspection position of the inspection target object 2 captured by the inspection visual sensor 4 (S31). Subsequently, the inspection machine learning unit 34 outputs the inspection result on the presence of defects of the inspection position of the inspection target object 2 on the basis of the image of the inspection position of the inspection target object 2 acquired by the image acquisition unit 17 according to the learnt learning model (S32).

As described above, according to the inspection device 10A and the inspection systems 1A and 1B of the first embodiment, when the inspector 3 performs visual inspection of the inspection target object 2, the line-of-sight information acquisition unit 11 acquires the line-of-sight information including the starting point of the line of sight, the line-of-sight direction, and the observation range of the inspector (FIGS. 3 and 4), the target object information acquisition unit 16 acquires the target object information including the position, attitude, and shape of the inspection target object, and the environmental information acquisition unit 22 acquires the environmental information including the type, the arrangement position, and the attitude of the illumination device 6. The construction label acquisition unit 24 acquires the design value (the type, the arrangement position, and the attitude of the inspection visual sensor 4, the type of the optical lens in the inspection visual sensor 4, the type, the arrangement position, and the attitude of the illumination device 6, the inspection assistance robot operation program, and the inspection program) of the inspection system for automating the visual inspection using the inspection visual sensor 4 as a label. The construction machine learning unit 26 learns a learning model using the line-of-sight information, the target object information, and the environmental information acquired during machine learning as input data and using the label as teaching data and outputs the design value of the inspection system on the basis of the line-of-sight information, the target object information, and the environmental information acquired during visual inspection after the machine learning ends (when the inspection system is constructed). The construction machine learning unit 26 (the program generation unit 28) specifies the observation position of the inspection target object 2 observed by the inspector during visual inspection as the inspection position on the basis of the line-of-sight information and the target object information acquired at the same timing. The program generation unit 28 generates the inspection assistance robot operation program for controlling the relative position between the inspection target object 2, the inspection visual sensor 4, and the illumination device 6 so that the image of the specified inspection position of the inspection target object 2 is captured using the inspection visual sensor 4. The program generation unit 28 generates an inspection program for inspecting the inspection target object 2 on the basis of the image of the inspection position of the inspection target object 2 captured using the inspection visual sensor 4. In this way, it is possible to automatically construct the inspection system easily.

According to the inspection device 10A and the inspection systems 1A and 1B of the first embodiment, when the inspection system is constructed, the environmental information output unit 30 outputs the information on the type, the arrangement position, and the attitude of the inspection visual sensor 4, the type of the optical lens in the inspection visual sensor 4, and the type, the arrangement position, and the attitude of the illumination device 6 as the environmental information in the setting value of the inspection system output by the construction machine learning unit 26. In this way, the inspector can prepare the inspection visual sensor 4, the optical lens in the inspection visual sensor 4, and the illumination device 6.

Second Embodiment

In the first embodiment, machine learning is performed to construct an inspection system. In the second embodiment, an inspection system is constructed without performing machine learning.

FIG. 10 is a diagram illustrating a configuration of an inspection device according to the second embodiment. An inspection device 10B illustrated in FIG. 10 corresponds to the inspection device 10 of the inspection systems 1A and 1B illustrated in FIGS. 1A and 1B respectively. The inspection device 10B is different from that of the first embodiment in that the inspection device 10B does not include the construction label acquisition unit 24, the construction machine learning unit 26, and the environmental information output unit 30 of the inspection device 10A illustrated in FIG. 2.

The environmental information acquisition unit 22 acquires the type, the arrangement position, and the attitude of the inspection visual sensor 4, the type of the optical lens in the inspection visual sensor 4, and the type, the arrangement position, and the attitude of the illumination device 6 as environmental information. These pieces of environmental information are input by the inspector.

The program generation unit 28 specifies the observation position of the inspection target object 2 observed by the inspector during visual inspection as the inspection position on the basis of the set of pieces of data including the line-of-sight information and the target object information acquired at the same timing during visual inspection. An observation point can be calculated as a point at which the line of sight of the inspector 3 crosses the surface of the inspection target object 2. When the observation range is provided around the observation point, it is the observation position. The program generation unit 28 generates the inspection assistance robot operation program for controlling the relative position between the inspection target object 2, the inspection visual sensor 4, and the illumination device 6 so that the image of the specified inspection position of the inspection target object 2 is captured using the inspection visual sensor 4. If the type of the inspection visual sensor 4 and the type of the optical lens are acquired in advance, it is possible to determine the distance between the inspection visual sensor 4 and the inspection target object 2 such that an entire inspection range appears in a captured image and a focusing state is created. The program generation unit 28 generates an inspection program for inspecting the inspection target object 2 on the basis of the captured image of the inspection position of the inspection target object 2. The inspection program may be generated according to predetermined rules, and the inspection program may be generated by supervised learning or unsupervised learning. For example, when a round hole is present in the inspection position, an inspection program for measuring the diameter of the hole can be generated.

Next, an inspection system construction operation performed by the inspection device 10B of the present embodiment will be described with reference to FIGS. 3, 4, and 11. FIG. 11 is a flowchart illustrating an inspection system construction operation performed by the inspection device 10B of the present embodiment.

First, as illustrated in FIG. 3, when the inspector 3 performs visual inspection of the inspection target object 2, an image of the vicinity of the eyes of the inspector 3 is captured by the line-of-sight visual sensor 5, and an image of the inspection target object 2 is captured by the target object visual sensor 4A. In this case, the inspector inputs the type, the arrangement position, and the attitude of the inspection visual sensor 4, the type of the optical lens in the inspection visual sensor 4, and the type, the arrangement position, and the attitude of the illumination device 6 to the inspection device 10B as the environmental information during visual inspection. As illustrated in FIG. 4, the inspector inputs an observation range (a fixed value) of the inspection target object 2 during visual inspection in advance.

The same operations as steps S11 and S12 in FIG. 6 are performed whereby the line-of-sight information acquisition unit 11 acquires the line-of-sight information including the starting point of the line of sight, the line-of-sight direction, and the observation range (a fixed value) of the inspector 3 during visual inspection (S11) and the target object information acquisition unit 16 acquires the target object information including the position, attitude, and shape of the inspection target object 2 during visual inspection (S12). The environmental information acquisition unit 22 acquires the type, the arrangement position, and the attitude of the inspection visual sensor 4, the type of the optical lens in the inspection visual sensor 4, and the type, the arrangement position, and the attitude of the illumination device 6 (the environmental information) input by the inspector (S43).

Subsequently, the program generation unit 28 specifies the observation position of the inspection target object 2 observed by the inspector during visual inspection as the inspection position on the basis of the set of pieces of data including the line-of-sight information and the target object information acquired during visual inspection (S45).

Subsequently, the program generation unit 28 generates the operation program of the inspection assistance robot for controlling the relative position between the inspection target object 2, the inspection visual sensor 4, and the illumination device 6 so that the image of the specified inspection position of the inspection target object 2 is captured from an appropriate field of view and an appropriate distance using the inspection visual sensor 4 (S46).

The program generation unit 28 generates an inspection program for inspecting the inspection target object 2 on the basis of the captured image of the inspection position of the inspection target object 2 (S47). When there are a number of inspection positions of the inspection target object 2, the program generation unit 28 generates the inspection assistance robot operation program and the inspection program so that all inspection positions are inspected sequentially.

The machine learning operation for allowing the inspection device 10B of the present embodiment to perform inspection is the same as steps S21 to S23 of FIG. 7, and the inspection operation performed by the inspection device 10B of the present embodiment is the same as steps S31 to S32 of FIG. 8.

As described above, according to the inspection device 10B and the inspection systems 1A and 1B of the second embodiment, when the inspector 3 performs visual inspection of the inspection target object 2, the line-of-sight information acquisition unit 11 acquires the line-of-sight information including the starting point of the line of sight, the line-of-sight direction, and the observation range of the inspector (FIGS. 3 and 4), the target object information acquisition unit 16 acquires the target object information including the position, attitude, and shape of the inspection target object, and the environmental information acquisition unit 22 acquires the environmental information including the type, the arrangement position, and the attitude of the inspection visual sensor 4, the type of the optical lens in the inspection visual sensor 4, and the type, the arrangement position, and the attitude of the illumination device 6. The program generation unit 28 specifies the observation position of the inspection target object 2 observed by the inspector during visual inspection as the inspection position on the basis of the set of pieces of data including the line-of-sight information and the target object information acquired during visual inspection. The program generation unit 28 generates the inspection assistance robot operation program for controlling the relative position between the inspection target object 2, the inspection visual sensor 4, and the illumination device 6 so that the image of the specified inspection position of the inspection target object 2 is captured using the inspection visual sensor 4. The program generation unit 28 generates an inspection program for inspecting the inspection target object 2 on the basis of the image of the inspection position of the inspection target object 2 captured using the inspection visual sensor 4. In this way, it is possible to automatically and easily construct the inspection system.

In the inspection device 10B and the inspection systems 1A and 1B of the second embodiment, the environmental information including the type, the arrangement position, and the attitude of the inspection visual sensor 4, the type of the optical lens in the inspection visual sensor 4, and the type, the arrangement position, and the attitude of the illumination device 6 are determined in advance, and the determined environmental information is input to the environmental information acquisition unit 22 of the inspection device 10B. Therefore, the inspector may prepare the inspection visual sensor 4, the optical lens in the inspection visual sensor 4, and the illumination device 6 on the basis of the environmental information. Here, during visual inspection, the inspector may incline the inspection target object 2 at an appropriate angle with respect to an incident light from the illumination device 6 so that defects (scratches, surface irregularity, or the like) present on the surface of the inspection position of the inspection target object 2 are easily recognized. Based on such environmental information, the program generation unit 28 generates a program so that the positional relationship between the inspection visual sensor 4, the inspection target object 2, and the illumination device 6 matches the positional relationship of these during the visual inspection. This will be described in detail below.

Figure 9A:
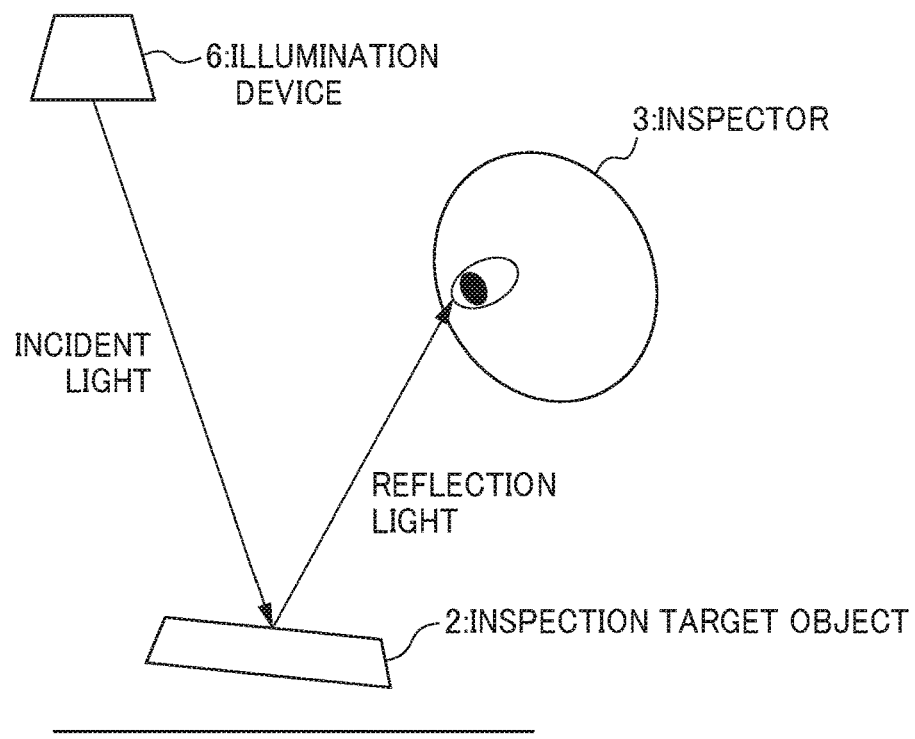
FIG. 9A is a diagram illustrating an example of a positional relationship between an inspector, an inspection target object, and an illumination device during visual inspection.
Figure 9B:
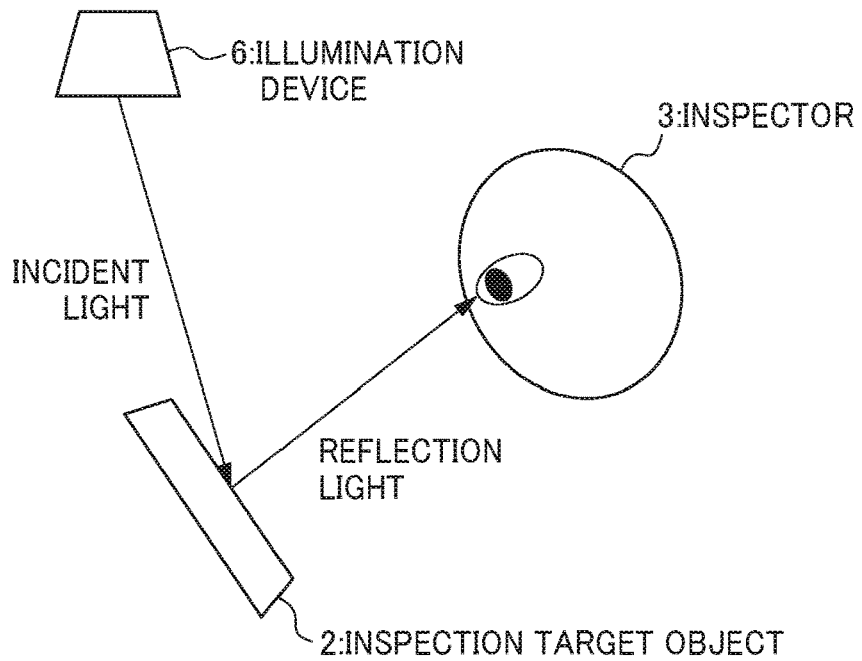
FIG. 9B is a diagram illustrating another example of a positional relationship between an inspector, an inspection target object, and an illumination device during visual inspection.
Figure 12:
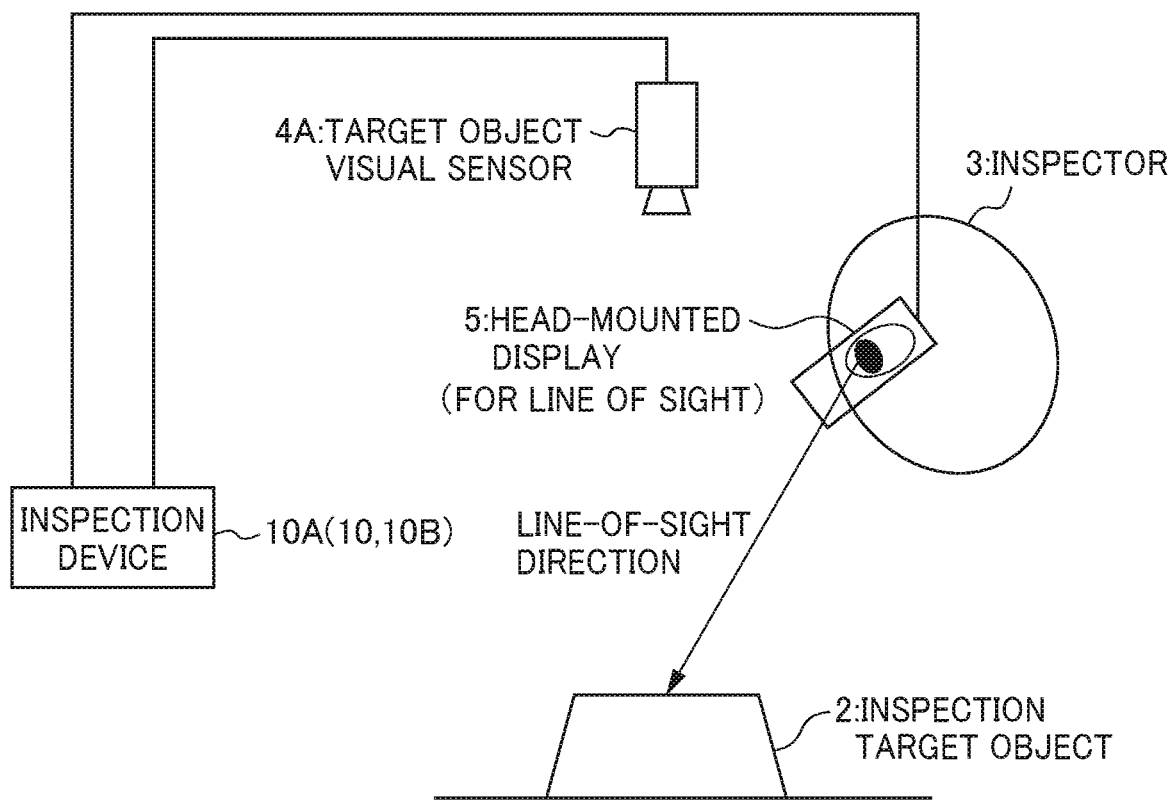
FIG. 12 is a schematic diagram for describing visual inspection.

As illustrated in FIG. 9A, during visual inspection, the inspector 3 inclines the inspection target object 2 at an appropriate angle with respect to an incident light from the illumination device 6 so that an appropriate reflection light is obtained from the inspection position of the inspection target object 2. In this way, the inspector can easily recognize defects (scratches, surface irregularity, or the like) present on the surface of the inspection position of the inspection target object 2. It is thought that similar effects are obtained by controlling the positional relationship between the inspection visual sensor 4, the inspection target object 2, and the illumination device 6 when capturing the image of the inspection target object 2 using the inspection visual sensor 4 so as to match the positional relationship between the inspector 3, the inspection target object 2, and the illumination device 6 during visual inspection. That is, it is thought that an image that makes inspection easy can be captured. In order to easily realize the positional relationship between the inspector 3, the inspection target object 2, and the illumination device 6 during visual inspection, the inspection device 10B may include the environmental information output unit 30 as described in FIG. 2 and the environmental information output unit 30 may output the type of the illumination device 6. For example, when the positional relationship between the inspector 3, the inspection target object 2, and the illumination device 6 during visual inspection illustrated in FIG. 9B is realized by the inspection system 1A or 1B illustrated in FIG. 1A or 1B, the environmental information output unit 30 outputs a low-angle illumination device different from the illumination device used during the visual inspection as the type of the illumination device 6. When the inspector prepares the illumination device output by the environmental information output unit 30, it is possible to easily realize the positional relationship between the inspector 3, the inspection target object 2, and the illumination device 6 during visual inspection even when capturing the image of the inspection target object 2 using the inspection visual sensor 4 and to improve the inspection efficiency.

While the embodiments of the present invention have been described, the present invention is not limited to the above-described embodiments. The effects described in the present embodiment are only examples of most preferable effects produced by the present invention, and the effects of the present invention are not limited to those described in the present embodiment.

For example, the above-described embodiments have illustrated an inspection device and an inspection system for inspecting for the presence of defects (for example, scratches on a surface or adhesion of foreign materials) of the inspection target object 2. However, the features of the present invention can be applied to various inspection systems that perform various inspections on an inspection target object on the basis of the image of the inspection target object captured by an imaging device such as a visual sensor. The features of the present invention can be applied to various inspection devices such as an inspection device that calculates a probability of presence of defects in the inspection target object 2 and an inspection device that outputs the position of defects of the inspection target object 2 without being limited to the inspection device that performs inspection (OK (no defects) or NG (with defects)) for presence of defects of the inspection target object 2 (the teaching data of a machine learning unit may be changed so that the inspection result to be output is changed).

In the above-described embodiments, the inspection system that includes a visual sensor for acquiring the line-of-sight information of the inspector and the target object information of the inspection target object during visual inspection has been illustrated. However, the inspection system may include various imaging devices such as a three-dimensional sensor instead of the visual sensor.

In the above-described embodiments, the inspection system may include a transmissive head-mounted display 5 illustrated in FIG. 11 instead of the line-of-sight visual sensor 5 illustrated in FIG. 3. The head-mounted display 5 has a function of specifying the position of an eyeball and the line-of-sight direction of the inspector 3. The head-mounted display 5 has a function of displaying an observation range on a display and a function of changing the size and shape of the observation range according to an operation of the inspector 3. The head-mounted display 5 outputs the specified eyeball position and the line-of-sight direction of the inspector 3 and the observation range on the display set by the inspector. In this way, the line-of-sight information acquisition unit 11 acquires the line-of-sight information including the starting point of the line of sight, the line-of-sight direction, and the observation range of the inspector 3 when the inspector 3 performs visual inspection for defects of the inspection target object 2. The timing at which the line-of-sight information is acquired may be a timing at which the inspector performs a certain operation and may be a timing at which a predetermined period is passed after the inspector observes the inspection target object. When the head-mounted display 5 is used, the detected position or type of the defects of the inspection target object 2 may be suggested on the head-mounted display 5. The target object visual sensor 4A may be mounted on the head-mounted display 5. The inspection position of the inspection target object will be in the facing direction of the face of the inspector. Due to this, the target object visual sensor 4A on the head-mounted display 5 can easily capture the image of the inspection position.

In the above-described embodiments, an aspect in which the line-of-sight information acquisition unit 11 and the target object information acquisition unit 16 include the image acquisition units 12 and 17 and the image processing units 13 and 18, respectively, has been illustrated. However, the line-of-sight information acquisition unit and the target object information acquisition unit may be configured without including the image processing unit. In this case, the image acquisition unit of the line-of-sight information acquisition unit may acquire the line-of-sight information obtained by the image processing unit of the line-of-sight visual sensor 5, and the image acquisition unit of the target object information acquisition unit may acquire the target object information obtained by the image processing unit of the target object visual sensor 4.

In the above-described embodiments, when a plurality of inspection positions is present in the inspection target object 2, different machine learning units may be provided in the respective inspection positions.

EXPLANATION OF REFERENCE NUMERALS 1A, 1B: Inspection system
2: Inspection target object
3: Inspector
4: Inspection visual sensor
4A: Target object visual sensor (target object imaging device)
5: Line-of-sight visual sensor (line-of-sight imaging device)
6: Illumination device
10, 10A, 10B: Inspection device
11: Line-of-sight information acquisition unit
12: Image acquisition unit
13: Image processing unit
16: Target object information acquisition unit
17: Image acquisition unit
18: Image processing unit
22: Environmental information acquisition unit
24: Construction label acquisition unit
26: Construction machine learning unit
28: Program generation unit
30: Environmental information output unit
32: Inspection label acquisition unit
34: Inspection machine learning unit
40: Storage unit
50: Inspection assistance robot
52: Arm
60: Robot controller

What is claimed is:

1. An inspection device that performs inspection of an inspection target object on the basis of an image of the inspection target object captured by an inspection imaging device, the inspection device comprising: a line-of-sight information acquisition unit that acquires line-of-sight information including a starting point of a line of sight, a line-of-sight direction, and an observation range of an inspector when the inspector performs visual inspection of the inspection target object;

a target object information acquisition unit that acquires target object information including a position, an attitude, and a shape of the inspection target object during the visual inspection; and a program generation unit that specifies an observation position of the inspection target object observed by the inspector during the visual inspection as an inspection position on the basis of a set of pieces of data including the line-of-sight information and the target object information, captures an image of the specified inspection position of the inspection target object using the inspection imaging device, and generates an inspection execution program for performing inspection of the inspection target object on the basis of the captured image of the inspection position of the inspection target object, wherein the inspection execution program uses an inspection assistance robot that holds the inspection target object or the inspection imaging device using an arm, and includes an operation program of the inspection assistance robot for controlling a relative position between the inspection target object and the inspection imaging device so that an image of the inspection position of the inspection target object is captured using the inspection imaging device, wherein the inspection device further comprising: an environmental information acquisition unit that acquires a type, an arrangement position, and an attitude of the inspection imaging device and a type of a lens in the inspection imaging device as environmental information, wherein the program generation unit generates an operation program of the inspection assistance robot for controlling the relative position between the inspection target object and the inspection imaging device on the basis of the environmental information.

2. An inspection system comprising: the inspection device according to claim 1;

an inspection imaging device that captures an image of an inspection target object;

a line-of-sight imaging device that captures an image of an inspector to obtain line-of-sight information of the inspector when the inspector performs visual inspection of the inspection target object;

a target object imaging device that captures an image of the inspection target object to obtain target object information of the inspection target object during the visual inspection;

an inspection assistance robot that holds the inspection target object or the inspection imaging device and controls a relative position between the inspection target object and the inspection imaging device;

a robot controller that controls the inspection assistance robot according to an operation program of the inspection assistance robot of the inspection execution program generated by the inspection device; and an illumination device that illuminates the inspection target object.

3. An inspection device that performs inspection of an inspection target object on the basis of an image of the inspection target object captured by an inspection imaging device, the inspection device comprising:

a line-of-sight information acquisition unit that acquires line-of-sight information including a starting point of a line of sight, a line-of-sight direction, and an observation range of an inspector when the inspector performs visual inspection of the inspection target object;

a target object information acquisition unit that acquires target object information including a position, an attitude, and a shape of the inspection target object during the visual inspection; and a program generation unit that specifies an observation position of the inspection target object observed by the inspector during the visual inspection as an inspection position on the basis of a set of pieces of data including the line-of-sight information and the target object information, captures an image of the specified inspection position of the inspection target object using the inspection imaging device, and generates an inspection execution program for performing inspection of the inspection target object on the basis of the captured image of the inspection position of the inspection target object, wherein the inspection execution program uses an inspection assistance robot that holds the inspection target object or the inspection imaging device using an arm, and includes an operation program of the inspection assistance robot for controlling a relative position between the inspection target object and the inspection imaging device so that an image of the inspection position of the inspection target object is captured using the inspection imaging device, wherein the inspection device further comprising: an environmental information acquisition unit that acquires at least one of a type, an arrangement position, and an attitude of an illumination device that illuminates the inspection target object as environmental information, wherein the program generation unit generates an operation program of the inspection assistance robot for controlling a relative position between the inspection target object, the inspection imaging device, and the illumination device on the basis of the environmental information.

4. An inspection device that performs inspection of an inspection target object on the basis of an image of the inspection target object captured by an inspection imaging device, the inspection device comprising:

a line-of-sight information acquisition unit that acquires line-of-sight information including a starting point of a line of sight, a line-of-sight direction, and an observation range of an inspector when the inspector performs visual inspection of the inspection target object;

a target object information acquisition unit that acquires target object information including a position, an attitude, and a shape of the inspection target object during the visual inspection;

a program generation unit that specifies an observation position of the inspection target object observed by the inspector during the visual inspection as an inspection position on the basis of a set of pieces of data including the line-of-sight information and the target object information, captures an image of the specified inspection position of the inspection target object using the inspection imaging device, and generates an inspection execution program for performing inspection of the inspection target object on the basis of the captured image of the inspection position of the inspection target object;

an environmental information acquisition unit that acquires environmental information on an environment during the visual inspection;

a construction label acquisition unit that acquires a design value of an inspection system for automating the visual inspection using the inspection imaging device as a label; and a construction machine learning unit that learns a learning model using the line-of-sight information acquired by the line-of-sight information acquisition unit, the target object information acquired by the target object information acquisition unit, and the environmental information acquired by the environmental information acquisition unit as input data and using the label acquired by the construction label acquisition unit as teaching data, wherein the construction machine learning unit outputs the design value of the inspection system according to the learnt learning model on the basis of the line-of-sight information acquired by the line-of-sight information acquisition unit, the target object information acquired by the target object information acquisition unit, and the environmental information acquired by the environmental information acquisition unit during the visual inspection.

5. The inspection device according to claim 4, wherein the inspection execution program uses an inspection assistance robot that holds the inspection target object or the inspection imaging device using an arm and includes an operation program of the inspection assistance robot for controlling a relative position between the inspection target object and the inspection imaging device so that an image of the inspection position of the inspection target object is captured using the inspection imaging device, the program generation unit includes the construction machine learning unit and specifies an observation position of the inspection target object observed by the inspector during the visual inspection as an inspection position on the basis of a set of pieces of data including the line-of-sight information and the target object information, and the program generation unit generates an operation program of the inspection assistance robot for controlling a relative position between the inspection target object and the inspection imaging device on the basis of the learning model learnt by the construction machine learning unit so that an image of the specified inspection position of the inspection target object is captured using the inspection imaging device.

6. The inspection device according to claim 5, wherein the environmental information includes at least one of a type, an arrangement position, and an attitude of an illumination device that illuminates the inspection target object, and the program generation unit generates an operation program of the inspection assistance robot for controlling a relative position between the inspection target object, the inspection imaging device, and the illumination device.

7. The inspection device according to claim 5, wherein the design value of the inspection system includes at least one of a type, an arrangement position, and an attitude of the inspection imaging device, a type of an optical lens in the inspection imaging device, a type, an arrangement position, and an attitude of an illumination device that illuminates the inspection target object, an operation program of the inspection assistance robot, and an inspection program, and the program generation unit generates an operation program of the inspection assistance robot for controlling a relative position between the inspection target object, the inspection imaging device, and the illumination device.

8. The inspection device according to claim 7, wherein the operation program included in the design value of the inspection system is a correction operation program obtained by correcting the operation program generated by the program generation unit.

9. The inspection device according to claim 5, further comprising: an environmental information output unit that outputs environmental information on an environment in the design value of the inspection system output from the construction machine learning unit, wherein the environmental information includes at least one of the type, the arrangement position, and the attitude of the inspection imaging device and the type of the lens in the inspection imaging device.

10. The inspection device according to claim 5, further comprising: an environmental information output unit that outputs environmental information on an environment in the design value of the inspection system output from the construction machine learning unit, wherein the environmental information includes at least one of the type, the arrangement position, and the attitude of the illumination device that illuminates the inspection target object.

* * * * *